United States Patent
Kostenis

(10) Patent No.: US 7,378,252 B2
(45) Date of Patent: May 27, 2008

(54) PROCESS FOR IDENTIFYING MODULATORS OF G-PROTEIN-COUPLED RECEPTORS

(75) Inventor: Evi Kostenis, Grebenau (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 313 days.

(21) Appl. No.: 11/060,023

(22) Filed: Feb. 17, 2005

(65) Prior Publication Data

US 2005/0255531 A1    Nov. 17, 2005

Related U.S. Application Data

(63) Continuation of application No. 09/899,295, filed on Jul. 6, 2001, now abandoned.

(30) Foreign Application Priority Data

Jul. 8, 2000    (DE)    ................................ 100 33 353

(51) Int. Cl.
*G01N 33/566*    (2006.01)

(52) U.S. Cl. ........................ 435/7.2; 435/7.21; 436/501

(58) Field of Classification Search ................. 435/7.1, 435/7.2, 7.21, 69.7; 536/23.4
See application file for complete search history.

(56) References Cited

FOREIGN PATENT DOCUMENTS

| WO | WO97/48820 | 12/1997 |
|---|---|---|
| WO | WO99/05177 | 2/1999 |

OTHER PUBLICATIONS

Conklin et al., Carboxyl-Terminal Mutations of Gqalpha and Gsalpha That Alter the Fidelity of Receptor Activation, Mol. Pharmacol., vol. 50, 1996, pp. 885-890.
Conklin et al., Substitution of Three Amino Acids Switches Receptor Specificity of Gqalpha to that of Gialpha, Nature, vol. 363, 1993, pp. 274-276.
Coward et al., Chimeric G Proteins Allow a High-Throughput Signaling Assay of G-coupled Receptors, Analytical Biochemistry, vol. 270, 1999, pp. 242-248.
Erlenbach et al., Single Amino Acid Substitutions and Deletions that Alter the G Protein Coupling Properties of the V2 Vasopessin Receptor Identified in Yeast by Receptor Random Mutagenesis, Journal of Biological Chemistry, vol. 276, 2001, pp. 29382-29392.
Kostenis et al., Functional Characterization of a Series of Mutant G Protein alphaq Subunits Displaying Promiscuous Receptor Coupling Properties, Journal of Biological Chemistry, vol. 273, 1998, pp. 17886-17892.
Kostenis et al., The N-terminal Extension of the Galphaq is Critical for Constraining the Selectivity of Receptor Coupling, Journal of Biological Chemistry, vol. 271, 1997, pp. 19107-19110.
MacDonald, C., Chapter 5: Primary culture and the establishment of cell lines, Basic Cell Culture, J.M. Davis, Ed., IRL Press, 1994, pp. 149-156.
McAteer et al., Chapter 4: Basic cell culture technique and the maintenance of cell lines, Basic Cell Culture, J.M. Davis, Ed., IRL Press 1994, pp. 93-122.
Migeon et al., Regulation of cAMP-mediated Gene Transcription by Wild Type and Mutated G-protein alpha Subunits, Journal of Biological Chemistry vol. 269, No. 46, 1994, pp. 29146-29152.
Wedegaertner et al., Palmitoylation is Required for Signaling Functions and Membrane Attachment of Gqalpha and Gsalpha, J. Biol. Chem, vol. 268, No. 33, 1993, pp. 25001-25008.

*Primary Examiner*—John Ulm
(74) *Attorney, Agent, or Firm*—Ann Marie Szczepanik

(57) ABSTRACT

The invention relates to a widely applicable process for identifying chemical compounds, which modulate G-protein-coupled receptors, by means of novel hybrid G-proteins with broad receptor specificity and very high expression and also to chemical compounds which can be identified by such a process.

36 Claims, 7 Drawing Sheets

Fig. 1

```
                                    αN Helix
             1       7 9 10      ―――――――――
αq (WTq)  MTLESIMAC.CLS......EEAK -
  -6q              MAC.CLS......EEAK -
αi1       MTLESMMAC.CLS......DEVK -

αi1,3              MGC.TLS......AEDK -
αo1,2              MGC.TLS......AEER -
αt1                MGA.GAS......AEEK -

αs                 MGCLGNSKTEDQRNEEK -
```

SEQUENCE LISTING

```
<160> NUMBER OF SEQ ID NOS: 17

<210> SEQ ID NO 1
<211> LENGTH: 1080
<212> TYPE: DNA
<213> ORGANISM: Mus musculus

<400> SEQUENCE: 1
atgactctgg agtccatcat ggcgtgctgc ctgagcgagg aggccaagga agcccggcgg      60
atcaacgacg agatcgagcg gcacgtccgc agggacaagc gggacgcccg ccgggagctc     120
aagctgctgc tgctcgggac aggagagagt ggcaagagta cgtttatcaa gcagatgaga     180
atcatccatg ggtcaggata ctctgatgaa gataaaaggg gcttcaccaa gctggtgtat     240
cagaacatct tcacggccat gcaggccatg atcgagcca tggacacact caagatccca     300
tacaagtatg agcacaataa ggctcatgca caattagttc gagaagttga tgtggagaag     360
```

-continued

```
gtgtctgctt ttgagaatcc atatgtagat gcaataaaga gtttatggaa tgatcctgga    420
atccaggaat gctatgatag acgacgagaa tatcaattat ctgactctac caaatactat    480
cttaatgact tggaccgcgt agctgaccct gcctacctgc ctacgcaaca agatgtgctt    540
agagttcgag tccccaccac agggatcatc gaataccct ttgacttaca aagtgtcatt     600
ttcagaatgg tcgatgtagg gggccaaagg tcagagagaa gaaaatggat acactgcttt    660
gaaaatgtca cctctatcat gtttctagta gcgcttagtg aatatgatca agttctcgtg    720
gagtcagaca atgagaaccg aatggaggaa agcaaggctc tctttagaac aattatcaca    780
taccccctggt tccagaactc ctcggttatt ctgttcttaa acaagaaaga tcttctagag    840
gagaaaatca tgtattccca tctagtcgac tacttcccag aatatgatgg accccagaga    900
gatgcccagg cagcccgaga attcattctg aagatgttcg tggacctgaa cccagacagt    960
gacaaaatta tctactccca cttcacgtgc gccacagaca ccgagaatat ccgctttgtc   1020
tttgctgccg tcaaggacac catcctccag ttgaacctga aggagtacaa tctggtctaa   1080
```

<210> SEQ ID NO 2
<211> LENGTH: 353
<212> TYPE: PRT
<213> ORGANISM: Mus musculus

<400> SEQUENCE: 2

```
Met Gly Cys Cys Leu Ser Glu Glu Ala Lys Glu Ala Arg Arg Ile Asn
 1               5                  10                  15
Asp Glu Ile Glu Arg His Val Arg Arg Asp Lys Arg Asp Ala Arg Arg
            20                  25                  30
Glu Leu Lys Leu Leu Leu Leu Gly Thr Gly Glu Ser Gly Lys Ser Thr
        35                  40                  45
Phe Ile Lys Gln Met Arg Ile Ile His Gly Ser Gly Tyr Ser Asp Glu
    50                  55                  60
Asp Lys Arg Gly Phe Thr Lys Leu Val Tyr Gln Asn Ile Phe Thr Ala
65                  70                  75                  80
Met Gln Ala Met Ile Arg Ala Met Asp Thr Leu Lys Ile Pro Tyr Lys
                85                  90                  95
Tyr Glu His Asn Lys Ala His Ala Gln Leu Val Arg Glu Val Asp Val
            100                 105                 110
Glu Lys Val Ser Ala Phe Glu Asn Pro Tyr Val Asp Ala Ile Lys Ser
        115                 120                 125
Leu Trp Asn Asp Pro Gly Ile Gln Glu Cys Tyr Asp Arg Arg Arg Glu
    130                 135                 140
Tyr Gln Leu Ser Asp Ser Thr Lys Tyr Tyr Leu Asn Asp Leu Asp Arg
145                 150                 155                 160
Val Ala Asp Pro Ala Tyr Leu Pro Thr Gln Gln Asp Val Leu Arg Val
                165                 170                 175
Arg Val Pro Thr Thr Gly Ile Ile Glu Tyr Pro Phe Asp Leu Gln Ser
            180                 185                 190
Val Ile Phe Arg Met Val Asp Val Gly Gly Gln Arg Ser Glu Arg Arg
        195                 200                 205
Lys Trp Ile His Cys Phe Glu Asn Val Thr Ser Ile Met Phe Leu Val
    210                 215                 220
Ala Leu Ser Glu Tyr Asp Gln Val Leu Val Glu Ser Asp Asn Glu Asn
225                 230                 235                 240
Arg Met Glu Glu Ser Lys Ala Leu Phe Arg Thr Ile Ile Thr Tyr Pro
                245                 250                 255
```

```
Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
    290                 295                 300

Lys Met Phe Val Asp Leu Asn Pro Asp Ser Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Cys Gly Leu
            340                 345                 350

Phe
```

<210> SEQ ID NO 3
<211> LENGTH: 1062
<212> TYPE: DNA
<213> ORGANISM: Mus musculus

<400> SEQUENCE: 3

```
atggggtgct gcctgagcga ggaggccaag gaagcccggc ggatcaacga cgagatcgag    60
cggcacgtcc gcagggacaa gcgggacgcc cgccgggagc tcaagctgct gctgctcggg   120
acaggagaga gtggcaagag tacgtttatc aagcagatga gaatcatcca tgggtcagga   180
tactctgatg aagataaaag gggcttcacc aagctggtgt atcagaacat cttcacggcc   240
atgcaggcca tgatcagagc catggacaca ctcaagatcc catacaagta tgagcacaat   300
aaggctcatg cacaattagt tcgagaagtt gatgtggaga ggtgtctgc ttttgagaat   360
ccatatgtag atgcaataaa gagtttatgg aatgatcctg aatccaggga atgctatgat   420
agacgacgag aatatcaatt atctgactct accaaatact atcttaatga cttggaccgc   480
gtagctgacc ctgcctacct gcctacgcaa caagatgtgc ttagagttcg agtccccacc   540
acagggatca tcgaataccc ctttgactta caaagtgtca ttttcagaat ggtcgatgta   600
gggggccaaa ggtcagagag aagaaaatgg atacactgct ttgaaaatgt cacctctatc   660
atgtttctag tagcgcttag tgaatatgat caagttctcg tggagtcaga caatgagaac   720
cgaatggagg aaagcaaggc tctctttaga acaattatca cataccctg gttccagaac   780
tcctcggtta ttctgttctt aaacaagaaa gatcttctag aggagaaaat catgtattcc   840
catctagtcg actacttccc agaatatgat ggaccccaga gagatgccca ggcagcccga   900
gaattcattc tgaagatgtt cgtggacctg aacccagaca gtgacaaaat tatctactcc   960
cacttcacgt gcgccacaga caccgagaat atccgctttg tctttgctgc cgtcaaggac  1020
accatcctcc agttgaacct gaaggagtgt ggcctcttct aa                    1062
```

<210> SEQ ID NO 4
<211> LENGTH: 353
<212> TYPE: PRT
<213> ORGANISM: Mus musculus

<400> SEQUENCE: 4

```
Met Gly Cys Cys Leu Ser Glu Glu Ala Lys Glu Ala Arg Arg Ile Asn
  1               5                  10                  15

Asp Glu Ile Glu Arg His Val Arg Arg Asp Lys Arg Asp Ala Arg Arg
            20                  25                  30
```

```
Glu Leu Lys Leu Leu Leu Gly Thr Gly Glu Ser Gly Lys Ser Thr
         35                  40                  45
Phe Ile Lys Gln Met Arg Ile Ile His Gly Ser Gly Tyr Ser Asp Glu
     50                  55                  60
Asp Lys Arg Gly Phe Thr Lys Leu Val Tyr Gln Asn Ile Phe Thr Ala
 65                  70                  75                  80
Met Gln Ala Met Ile Arg Ala Met Asp Thr Leu Lys Ile Pro Tyr Lys
                 85                  90                  95
Tyr Glu His Asn Lys Ala His Ala Gln Leu Val Arg Glu Val Asp Val
                100                 105                 110
Glu Lys Val Ser Ala Phe Glu Asn Pro Tyr Val Asp Ala Ile Lys Ser
            115                 120                 125
Leu Trp Asn Asp Pro Gly Ile Gln Glu Cys Tyr Asp Arg Arg Arg Glu
        130                 135                 140
Tyr Gln Leu Ser Asp Ser Thr Lys Tyr Tyr Leu Asn Asp Leu Asp Arg
145                 150                 155                 160
Val Ala Asp Pro Ala Tyr Leu Pro Thr Gln Gln Asp Val Leu Arg Val
                165                 170                 175
Arg Val Pro Thr Thr Gly Ile Ile Glu Tyr Pro Phe Asp Leu Gln Ser
                180                 185                 190
Val Ile Phe Arg Met Val Asp Val Gly Gly Gln Arg Ser Glu Arg Arg
            195                 200                 205
Lys Trp Ile His Cys Phe Glu Asn Val Thr Ser Ile Met Phe Leu Val
        210                 215                 220
Ala Leu Ser Glu Tyr Asp Gln Val Leu Val Glu Ser Asp Asn Glu Asn
225                 230                 235                 240
Arg Met Glu Glu Ser Lys Ala Leu Phe Arg Thr Ile Ile Thr Tyr Pro
                245                 250                 255
Trp Phe Gln Asn Ser Ser Val Ile Leu Phe Leu Asn Lys Lys Asp Leu
                260                 265                 270
Leu Glu Glu Lys Ile Met Tyr Ser His Leu Val Asp Tyr Phe Pro Glu
            275                 280                 285
Tyr Asp Gly Pro Gln Arg Asp Ala Gln Ala Ala Arg Glu Phe Ile Leu
        290                 295                 300
Lys Met Phe Val Asp Leu Asn Pro Asp Ser Asp Lys Ile Ile Tyr Ser
305                 310                 315                 320
His Phe Thr Cys Ala Thr Asp Thr Glu Asn Ile Arg Phe Val Phe Ala
                325                 330                 335
Ala Val Lys Asp Thr Ile Leu Gln Leu Asn Leu Lys Gln Tyr Glu Leu
                340                 345                 350
Leu

<210> SEQ ID NO 5
<211> LENGTH: 1062
<212> TYPE: DNA
<213> ORGANISM: Mus musculus

<400> SEQUENCE: 5
atggcgtgct gcctgagcga ggaggccaag gaagcccggc ggatcaacga cgagatcgag    60
cggcacgtcc gcagggacaa gcgggacgcc cgccggagc tcaagctgct gctgctcggg   120
acaggagaga gtggcaagag tacgtttatc aagcagatga gaatcatcca tgggtcagga   180
tactctgatg aagataaaag gggcttcacc aagctggtgt atcagaacat cttcacggcc   240
atgcaggcca tgatcagagc catggacaca ctcaagatcc catacaagta tgagcacaat   300
```

```
aaggctcatg cacaattagt tcgagaagtt gatgtggaga aggtgtctgc ttttgagaat    360
ccatatgtag atgcaataaa gagtttatgg aatgatcctg gaatccagga atgctatgat    420
agacgacgag aatatcaatt atctgactct accaaatact atcttaatga cttggaccgc    480
gtagctgacc ctgcctacct gcctacgcaa caagatgtgc ttagagttcg agtccccacc    540
acagggatca tcgaataccc ctttgactta caaagtgtca ttttcagaat ggtcgatgta    600
gggggccaaa ggtcagagag aagaaaatgg atacactgct ttgaaaatgt cacctctatc    660
atgtttctag tagcgcttag tgaatatgat caagttctcg tggagtcaga caatgagaac    720
cgaatggagg aaagcaaggc tctctttaga acaattatca catacccctg gttccagaac    780
tcctcggtta ttctgttctt aaacaagaaa gatcttctag aggagaaaat catgtattcc    840
catctagtcg actacttccc agaatatgat ggaccccaga gagatgccca ggcagcccga    900
gaattcattc tgaagatgtt cgtggacctg aacccagaca gtgacaaaat tatctactcc    960
cacttcacgt gcgccacaga caccgagaat atccgctttg tctttgctgc cgtcaaggac   1020
accatcctcc agttgaacct gaaggagtgt ggcctcttct aa                      1062
```

```
<210> SEQ ID NO 6
<211> LENGTH: 353
<212> TYPE: PRT
<213> ORGANISM: Mus musculus

<400> SEQUENCE: 6

Met Ala Cys Cys Leu Ser Glu Glu Ala Lys Glu Ala Arg Arg Ile Asn
 1               5                  10                  15

Asp Glu Ile Glu Arg His Val Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
 65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
               100                 105                 110

Glu Lys Val Ser Ala Phe Glu Asn Pro Tyr Val Asp Ala Ile Lys Ser
            115                 120                 125

Leu Trp Asn Asp Pro Gly Ile Gln Glu Cys Tyr Asp Arg Arg Arg Glu
        130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240
```

-continued

```
Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
    290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Cys Gly Leu
            340                 345                 350

Phe
```

<210> SEQ ID NO 7
<211> LENGTH: 1062
<212> TYPE: DNA
<213> ORGANISM: Mus musculus

<400> SEQUENCE: 7

```
atggcgtgct gcctgagcga ggaggccaag gaagcccggc ggatcaacga cgagatcgag     60
cggcacgtcc gcagggacaa gcgggacgcc gccggagc tcaagctgct gctgctcggg       120
acaggagaga gtggcaagag tacgtttatc aagcagatga aatcatcca tgggtcagga     180
tactctgatg aagataaaag gggcttcacc aagctggtgt atcagaacat cttcacggcc     240
atgcaggcca tgatcagagc catggacaca ctcaagatcc catacaagta tgagcacaat     300
aaggctcatg cacaattagt tcgagaagtt gatgtgttga aggtgtctgc ttttgagaat     360
ccatatgtag atgcaataaa gagtttatgg aatgatcctg aatccaggga atgctatgat     420
agacgacgag aatatcaatt atctgactct accaaatact atcttaatga cttggaccgc     480
gtagctgacc ctgcctacct gcctacgcaa caagatgtgc ttagagttcg agtccccacc     540
acagggatca tcgaataccc cttttgactta caaagtgtca tttttcagaat ggtcgatgta     600
gggggcaaa ggtcagagag aagaaatg atacactgct ttgaaatgt cacctctatc     660
atgtttctag tagcgcttag tgaatatgat caagttctcg tggagtcaga caatgagaac     720
cgaatggagg aaagcaaggc tctctttaga acaattatca catacccctg gttccagaac     780
tcctcggtta ttctgttctt aaacaagaaa gatcttctag aggagaaaat catgtattcc     840
catctagtcg actacttccc agaatatgat ggaccccaga gagatgccca ggcagcccga     900
gaattcattc tgaagatgtt cgtggacctg aacccagaca gtgacaaaat tatctactcc     960
cacttcacgt gcgccacaga caccgagaat atccgctttg tctttgctgc cgtcaaggac    1020
accatcctcc agttgaacct gaaggagtgt ggcctcttct aa                       1062
```

<210> SEQ ID NO 8
<211> LENGTH: 353
<212> TYPE: PRT
<213> ORGANISM: Mus musculus

<400> SEQUENCE: 8

```
Met Ala Cys Cys Leu Ser Glu Glu Ala Lys Glu Ala Arg Arg Ile Asn
  1               5                  10                  15
```

```
Asp Glu Ile Glu Arg His Val Arg Arg Asp Lys Arg Asp Ala Arg Arg
            20                  25                  30

Glu Leu Lys Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
 65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
                100                 105                 110

Glu Lys Val Ser Ala Phe Glu Asn Pro Tyr Val Asp Ala Ile Lys Ser
            115                 120                 125

Leu Trp Asn Asp Pro Gly Ile Gln Glu Cys Tyr Asp Arg Arg Arg Glu
130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
                180                 185                 190

Val Ile Phe Arg Met Val Asp Val Gly Gly Gln Arg Ser Glu Arg Arg
                195                 200                 205

Lys Trp Ile His Cys Phe Glu Asn Val Thr Ser Ile Met Phe Leu Val
210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
                260                 265                 270

Leu Glu Glu Lys Ile Met Tyr Ser His Leu Val Asp Tyr Phe Pro Glu
            275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Gln Tyr Glu Leu
            340                 345                 350

Leu

<210> SEQ ID NO 9
<211> LENGTH: 1128
<212> TYPE: DNA
<213> ORGANISM: Mus musculus

<400> SEQUENCE: 9
gccatggccc gctcgctgac ctggcgctgc tgcccctggt gcctgacgga ggatgagaag      60
gccgccgccc gggtggacca ggagatcaac aggatcctct ggagcagaa gaagcaggac      120 cgcggggagc tgaagctgct gcttttgggc ccaggcgaga gcgggaagag caccttcatc     180
```

```
aagcagatgc ggatcatcca cggcgccggc tactcggagg aggagcgcaa gggcttccgg      240
cccctggtct accagaacat cttcgtgtcc atgcgggcca tgatcgaggc catggagcgg      300
ctgcagattc cattcagcag gcccgagagc aagcaccacg ctagcctggt catgagccag      360 gaccccctata aagtgaccac gtttgagaag cgctacgctg cggccatgca gtggctgtgg      420
agggatgccg gcatccgggc ctgctatgag cgtcggcggg aattccacct gctcgattca      480
gccgtgtact acctgtccca cctggagcgc atcaccgagg agggctacgt ccccacagct      540
caggacgtgc tccgcagccg catgcccacc actggcatca acgagtactg cttctccgtg      600
cagaaaacca acctgcggat cgtggacgtc ggggggccaga agtcagagcg taagaaatgg      660
atccattgtt tcgagaacgt gatcgccctc atctacctgg cctcactgag tgaatacgac      720
cagtgcctgg aggagaacaa ccaggagaac cgcatgaagg agagcctcgc attgtttggg      780
actatcctgg aactaccctg gttcaaaagc acatccgtca tcctctttct caacaaaacc      840
gacatcctgg aggagaaaat ccccacctcc cacctggcta cctatttccc cagttttccag     900 ggccctaagc aggatgctga ggcagccaag aggttcatcc tggacatgta cacgaggatg      960
tacaccgggt gcgtggacgg ccccgagggc agcaagaagg gcgcacgatc ccgacgcctt      1020
ttcagccact acacatgtgc cacagacaca cagaacatcc gcaaggtctt caaggacgtg      1080
cgggactcgg tgctcgcccg ctacctggac gagatcaacc tgctgtga                 1128
```

<210> SEQ ID NO 10
<211> LENGTH: 374
<212> TYPE: PRT
<213> ORGANISM: Mus musculus

<400> SEQUENCE: 10

```
Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205
```

```
Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
        355                 360                 365

Asp Glu Ile Asn Leu Leu
    370

<210> SEQ ID NO 11
<211> LENGTH: 359
<212> TYPE: PRT
<213> ORGANISM: Mus musculus

<400> SEQUENCE: 11

Met Thr Leu Glu Ser Ile Met Ala Cys Cys Leu Ser Glu Glu Ala Lys
  1               5                  10                  15

Glu Ala Arg Arg Ile Asn Asp Glu Ile Glu Arg His Val Arg Arg Asp
                 20                  25                  30

Lys Arg Asp Ala Arg Arg Glu Leu Lys Leu Leu Leu Leu Gly Thr Gly
             35                  40                  45

Glu Ser Gly Lys Ser Thr Phe Ile Lys Gln Met Arg Ile Ile His Gly
         50                  55                  60

Ser Gly Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205
```

```
Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
            275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
            355

<210> SEQ ID NO 12
<211> LENGTH: 353
<212> TYPE: PRT
<213> ORGANISM: Mus musculus

<400> SEQUENCE: 12

Met Ala Cys Cys Leu Ser Glu Glu Ala Lys Glu Ala Arg Arg Ile Asn
1               5                   10                  15

Asp Glu Ile Glu Arg His Val Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
                100                 105                 110

Glu Lys Val Ser Ala Phe Glu Asn Pro Tyr Val Asp Ala Ile Lys Ser
            115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
                180                 185                 190

Val Ile Phe Arg Met Val Asp Val Gly Gly Gln Arg Ser Glu Arg Arg
            195                 200                 205

Lys Trp Ile His Cys Phe Glu Asn Val Thr Ser Ile Met Phe Leu Val
```

```
            210                 215                 220
Ala Leu Ser Glu Tyr Asp Gln Val Leu Val Ser Asp Asn Glu Asn
225                 230                 235                 240

Arg Met Glu Glu Ser Lys Ala Leu Phe Arg Thr Ile Ile Thr Tyr Pro
                    245                 250                 255

Trp Phe Gln Asn Ser Ser Val Ile Leu Phe Leu Asn Lys Lys Asp Leu
                    260                 265                 270

Leu Glu Glu Lys Ile Met Tyr Ser His Leu Val Asp Tyr Phe Pro Glu
                275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                    325                 330                 335

Ala Val Lys Asp Thr Ile Leu Gln Leu Asn Leu Lys Glu Tyr Asn Leu
                340                 345                 350

Val

<210> SEQ ID NO 13
<211> LENGTH: 359
<212> TYPE: PRT
<213> ORGANISM: Mus musculus

<400> SEQUENCE: 13

Met Thr Leu Glu Ser Met Met Ala Cys Cys Leu Ser Asp Glu Val Lys
 1               5                  10                  15

Glu Ala Arg Arg Ile Asn Asp Glu Ile Glu Arg His Val Arg Arg Asp
                20                  25                  30

Lys Arg Asp Ala Arg Arg Glu Leu Lys Leu Leu Leu Leu Gly Thr Gly
            35                  40                  45

Glu Ser Gly Lys Ser Thr Phe Ile Lys Gln Met Arg Ile Ile His Gly
        50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                    85                  90                  95

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Glu Asn Pro Tyr
            115                 120                 125

Val Asp Ala Ile Lys Ser Leu Trp Asn Asp Pro Gly Ile Gln Glu Cys
        130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
```

```
                225                 230                 235                 240
Glu Ser Asp Asn Glu Asn Arg Met Glu Glu Ser Lys Ala Leu Phe Arg
                    245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
                275                 280                 285

Val Asp Tyr Phe Pro Glu Tyr Asp Gly Pro Gln Arg Asp Ala Gln Ala
                290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
                355

<210> SEQ ID NO 14
<211> LENGTH: 353
<212> TYPE: PRT
<213> ORGANISM: Mus musculus

<400> SEQUENCE: 14

Met Gly Cys Thr Leu Ser Ala Glu Asp Lys Glu Ala Arg Arg Ile Asn
1               5                   10                  15

Asp Glu Ile Glu Arg His Val Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
                100                 105                 110

Glu Lys Val Ser Ala Phe Glu Asn Pro Tyr Val Asp Ala Ile Lys Ser
            115                 120                 125

Leu Trp Asn Asp Pro Gly Ile Gln Glu Cys Tyr Asp Arg Arg Arg Glu
        130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
                180                 185                 190

Val Ile Phe Arg Met Val Asp Val Gly Gly Gln Arg Ser Glu Arg Arg
            195                 200                 205

Lys Trp Ile His Cys Phe Glu Asn Val Thr Ser Ile Met Phe Leu Val
        210                 215                 220

Ala Leu Ser Glu Tyr Asp Gln Val Leu Val Glu Ser Asp Asn Glu Asn
225                 230                 235                 240
```

```
Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
    290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
            340                 345                 350

Val

<210> SEQ ID NO 15
<211> LENGTH: 353
<212> TYPE: PRT
<213> ORGANISM: Mus musculus

<400> SEQUENCE: 15

Met Gly Cys Thr Leu Ser Ala Glu Glu Arg Glu Ala Arg Arg Ile Asn
 1               5                  10                  15

Asp Glu Ile Glu Arg His Val Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
                100                 105                 110

Glu Lys Val Ser Ala Phe Glu Asn Pro Tyr Val Asp Ala Ile Lys Ser
            115                 120                 125

Leu Trp Asn Asp Pro Gly Ile Gln Glu Cys Tyr Asp Arg Arg Arg Glu
        130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
                180                 185                 190

Val Ile Phe Arg Met Val Asp Val Gly Gly Gln Arg Ser Glu Arg Arg
            195                 200                 205

Lys Trp Ile His Cys Phe Glu Asn Val Thr Ser Ile Met Phe Leu Val
        210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255
```

```
Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
                340                 345                 350

Val

<210> SEQ ID NO 16
<211> LENGTH: 353
<212> TYPE: PRT
<213> ORGANISM: Mus musculus

<400> SEQUENCE: 16

Met Gly Ala Gly Ala Ser Ala Glu Glu Lys Glu Ala Arg Arg Ile Asn
1               5                   10                  15

Asp Glu Ile Glu Arg His Val Arg Arg Asp Lys Arg Asp Ala Arg Arg
            20                  25                  30

Glu Leu Lys Leu Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Glu Asn Pro Tyr Val Asp Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270
```

```
Leu Glu Glu Lys Ile Met Tyr Ser His Leu Val Asp Tyr Phe Pro Glu
            275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
                340                 345                 350

Val

<210> SEQ ID NO 17
<211> LENGTH: 360
<212> TYPE: PRT
<213> ORGANISM: Mus musculus

<400> SEQUENCE: 17

Met Gly Cys Leu Gly Asn Ser Lys Thr Glu Asp Gln Arg Asn Glu Glu
1               5                   10                  15

Lys Glu Ala Arg Arg Ile Asn Asp Glu Ile Glu Arg His Val Arg Arg
            20                  25                  30

Asp Lys Arg Asp Ala Arg Arg Glu Leu Lys Leu Leu Leu Leu Gly Thr
        35                  40                  45

Gly Glu Ser Gly Lys Ser Thr Phe Ile Lys Gln Met Arg Ile Ile His
    50                  55                  60

Gly Ser Gly Tyr Ser Asp Glu Asp Lys Arg Gly Phe Thr Lys Leu Val
65                  70                  75                  80

Tyr Gln Asn Ile Phe Thr Ala Met Gln Ala Met Ile Arg Ala Met Asp
                85                  90                  95

Thr Leu Lys Ile Pro Tyr Lys Tyr Glu His Asn Lys Ala His Ala Gln
            100                 105                 110

Leu Val Arg Glu Val Asp Val Glu Lys Val Ser Ala Phe Glu Asn Pro
        115                 120                 125

Tyr Val Asp Ala Ile Lys Ser Leu Trp Asn Asp Pro Gly Ile Gln Glu
    130                 135                 140

Cys Tyr Asp Arg Arg Arg Glu Tyr Gln Leu Ser Asp Ser Thr Lys Tyr
145                 150                 155                 160

Tyr Leu Asn Asp Leu Asp Arg Val Ala Asp Pro Ala Tyr Leu Pro Thr
                165                 170                 175

Gln Gln Asp Val Leu Arg Val Arg Val Pro Thr Thr Gly Ile Ile Glu
            180                 185                 190

Tyr Pro Phe Asp Leu Gln Ser Val Ile Phe Arg Met Val Asp Val Gly
        195                 200                 205

Gly Gln Arg Ser Glu Arg Arg Lys Trp Ile His Cys Phe Glu Asn Val
    210                 215                 220

Thr Ser Ile Met Phe Leu Val Ala Leu Ser Glu Tyr Asp Gln Val Leu
225                 230                 235                 240

Val Glu Ser Asp Asn Glu Asn Arg Met Glu Glu Ser Lys Ala Leu Phe
                245                 250                 255

Arg Thr Ile Ile Thr Tyr Pro Trp Phe Gln Asn Ser Ser Val Ile Leu
            260                 265                 270

Phe Leu Asn Lys Lys Asp Leu Leu Glu Glu Lys Ile Met Tyr Ser His
        275                 280                 285
```

-continued

```
Leu Val Asp Tyr Phe Pro Glu Tyr Asp Gly Pro Gln Arg Asp Ala Gln
    290             295             300

Ala Ala Arg Glu Phe Ile Leu Lys Met Phe Val Asp Leu Asn Pro Asp
305             310             315             320

Ser Asp Lys Ile Ile Tyr Ser His Phe Thr Cys Ala Thr Asp Thr Glu
                325             330             335

Asn Ile Arg Phe Val Phe Ala Ala Val Lys Asp Thr Ile Leu Gln Leu
            340             345             350

Asn Leu Lys Glu Tyr Asn Leu Val
        355             360
```

US 7,378,252 B2

PROCESS FOR IDENTIFYING MODULATORS OF G-PROTEIN-COUPLED RECEPTORS

RELATED APPLICATIONS

This application is a continuation of U.S. patent application Ser. No. 09/899,295 filed on Jul. 6, 2001, now abandoned, which claims the benefit of German Patent Application No. 10033353.2 filed Jul. 8, 2000, all of which are incorporated herein by reference.

TECHNICAL FIELD

The invention relates to a process for identifying chemical compounds which modulate G-protein-coupled receptors, by means of novel hybrid G-proteins with broad receptor specificity, and also to chemical compounds which can be identified by such a process

BACKGROUND OF THE INVENTION

G-protein-coupled receptors (GPCRs) play an important role in a multiplicity of physiological processes. They are one of the most important protein families known to date, and it is assumed that in the human genome about 1000 genes code for members of this receptor class. GPCRs have a characteristic structure: they are peptide threads which meander in the form of α-helices seven times through the phospholipid bilayer of the cell membrane, arranging themselves in a circle. It is estimated that about 60% of the pharmaceuticals presently available through prescription bind to GPCRs. This underlines the importance of this receptor class to the pharmaceutical research industry.

G-protein-coupled receptors share a common mechanism of action. Binding of an extracellular ligand leads to a conformational change in the receptor protein that allows it to make contact with a guanine-nucleotide binding protein (G-protein). G-proteins are located on the cytoplasmic side of the plasma membrane and mediate the extracellular signal in the cell interior to trigger various intracellular reactions.

GPCRs are the most important therapeutic target proteins to date. An estimated 40% of the pharmaceuticals prescribed by doctors act as agonists or antagonists of GPCRs. Owing to the size and importance of this protein family and in view of the fact that chemical binding partners for many GPCRs are unknown (orphan GPCRs), it can be assumed that this receptor class will be one of the most important reservoirs for suitable target proteins in the search for novel medicinal substances in the future.

GPCRs are integral membrane proteins that transfer a signal mediated via a mostly hydrophilic signal substance bound to the outer side of the cell into the cell interior via a family of G-proteins. Depending on the receptor specificity and the G-proteins activated thereby, activated GPCRs trigger various signal transduction pathways. Depending on the receptor type, various actions are evoked, all of which lead to the formation of second messengers. Second messengers are intracellular messenger molecules, such as, for example, cAMP, cGMP, and $Ca^{2+}$, formed in or released into the cytosol in response to an extracellular signal and which trigger reactions in the cell through the activation or deactivation of intracellular proteins. Thus, activation of a membrane-bound adenylate cyclase may lead to an increase in the intracellular cAMP level, and inhibition may lead to a decrease. Stimulation of a cGMP-specific phosphodiesterase may lead to a reduction in the cGMP level. The activated G-protein can also lead, for example, to an increase of $Ca^{2+}$ or $K^+$ ions by binding to an ion channel. Furthermore, an activated G-protein can affect activation of a phospholipase and thus formation of inositol 1,4,5-trisphosphate and diacylglycerol. This, in turn, leads either to a $Ca^{2+}$ increase or to activation of a protein kinase C, with further effects in both cases.

The heterotrimeric G-proteins are located on the inside of the plasma membrane. They comprise the three subunits α, β and γ. When an activated receptor makes contact with the G-protein heterotrimer, it dissociates into an α subunit and a βγ complex. Both the activated α subunit and the βγ complex can influence intracellular effector proteins. The G-protein α subunit family is presently divided into four different classes (Gαs, Gαi, Gαq and Gα12 classes).

GPCRs are classified according to the G-proteins that they contact. GPCRs of the Gs class mediate adenylate cyclase stimulation via activation of Gαs and increase the intracellular cAMP concentration. GPCRs of the Gi class mediate adenylate cyclase inhibition via activation of Gαi and decrease intracellular cAMP. GPCRs of the Gq class mediate stimulation of various phospholipase C beta (PLCβ) isoforms via activation of Gαq and lead to hydrolysis of membrane-bound phosphatidylinositol 4,5-bisphosphate to give diacylglycerol and inositol 1,4,5-trisphosphate (IP3). IP3 releases $Ca^{2+}$ from intracellular depots.

Most GPCRs can make contact only with one G-protein α subunit family, and, therefore, are selective for a particular signal transduction pathway. This narrow specificity is a great hindrance to the identification of chemical compounds capable of modulating GPCR-dependent signal transduction pathways.

Moreover, a suitable signal which can be utilized in a screening assay with high sample throughput is obtained only from those signal transduction pathways in which, for example, G-protein activation leads to an increase in the intracellular $Ca^{2+}$ level.

Hybrid G-proteins with altered receptor specifity and signal transduction pathway linkage may be constructed by joining together parts of various G-proteins using known molecular biology and biochemistry methods.

Hybrid G-proteins are fusion constructs which combine sequences of various Gα subunits within one protein. Thus it is possible, for example by fusion of the Gαi receptor recognition region to the Gαq effector activation region, to prepare a Gαq/i hybrid which receives signals from Gi-coupled receptors but switches on the Gαq-PLCβ signal transduction pathway. Such a hybrid, in which the C-terminal 5 amino acids of Gαq is replaced by the corresponding Gαi sequence (Gαqi5), was first described by Conklin et al., Nature 363, 274-276 (1993).

This "recoupling" of receptors has the advantage that the assay endpoint (increase in intracellular $Ca^{2+}$ concentration in comparison with adenylate cyclase inhibition) is more readily accessible through measurement methods and can be used in high throughput screening.

However, the disadvantage of the Gαq/Gαi fusion constructs is that they are unable to activate some GPCRs, such as, for example, the SSTR1 receptor qi5 (Conklin et al., Mol. Pharmacol. 50, 885-890 (1996)).

Similarly, fusion constructs between Gαq and Gαs have been described. These too have the disadvantage that they cannot link all Gs-coupled receptors to the PLCβ signal transduction pathway, such as the β2-adrenergic receptor and the dopamine D1 receptor, for example.

Besides C-terminal modifications for altering the linking of receptors to particular signal transduction pathways, an N-terminal modification of Gαq has been described which allows the G-protein to receive and pass on signals from several different receptors. In this Gαq protein, the 6 highly conserved N-terminal amino acids were deleted (Kostenis et al., J. Biol. Chem. 272, 19107-19110 (1997)). This deletion allows the resulting Gq (also called –6q) to receive signals not only from Gq- but also from Gs- or Gi/o-coupled receptors and to pass them on to PLCβ.

This mutant Gα subunit also recognizes receptors such as the SSTR1 somatostatin receptor, the dopamine D1 receptor and the adrenergic β2 receptor. However, even this mutant is unable to recognize the receptor edg5. Moreover, the signal intensity of this mutant is so weak that it is unusable in practice (Kostenis et al., J. Biol. Chem. 272, 19107-19110 (1997)).

Another known Gα subunit is Gα16 which links GPCRs from various functional classes to the PLCβ-$Ca^{2+}$ signal transduction pathway. Gα16 is a G-protein with broad receptor specificity and has been disclosed in WO 97/48820 (title: Promiscuous G-protein compositions and their use). Gα16 is practically nonselective by nature. But even this subunit is not universally applicable, because receptors such as the edg5 receptor or the SSTR1 somatostatin receptor couple to it only weakly, if at all.

Thus, it would be very useful if a G-protein were available that could be activated by other functional GPCR classes, could also give a sufficiently strong signal in the cell. Such a G-protein could be utilized in a screening assay, such as a high throughput screening assay, to identify compounds modulating GPCRs and/or the appropriate dependent signal transduction pathways, for example a signal such as the increase or decrease in the intracellular $Ca^{2+}$ concentration.

The object of the present invention is therefore to provide further hybrid G-proteins characterized by having recognizable broad specificity with respect to GPCRs. These G-proteins can be used in screening processes to identify chemical compounds by the coupling of the G-proteins to a signal pathway leading to an increase in the intracellular $Ca^{2+}$ concentration. In addition, these proteins can be expressed at such a high level that signal intensity is improved.

SUMMARY OF THE INVENTION

The invention relates to a process for identifying a chemical compound modifying the action of at least one G-protein-coupled receptor (GPCR)-dependent signal transduction pathway of an organism, wherein said process comprises:
 a) providing at least one cell which contains at least one GPCR-dependent signal transduction pathway and which produces one or more than one G-protein;
 b) providing at least one chemical compound to be studied;
 c) contacting the cell or cells of a) with one or more chemical compounds of b);
 d) determining the quantitative or qualitative effect of the chemical compounds of b) on the signal transduction pathway of the cells of a) by means of a signal transduction pathway-dependent measurable signal.

BRIEF DESCRIPTION OF THE DRAWINGS

FIG. 1 represents an alignment of the amino-terminal regions of various Gα proteins (αq (WTq), SEQ ID NO:11;–6q, SEQ ID NO:12;α11, SEQ ID NO:13;αi1,3, SEQ ID NO;14;αo1,2, SEQ ID NO;15;αs, SEQ ID NO:16).

DETAILED DESCRIPTION OF THE INVENTION

Figure 2:
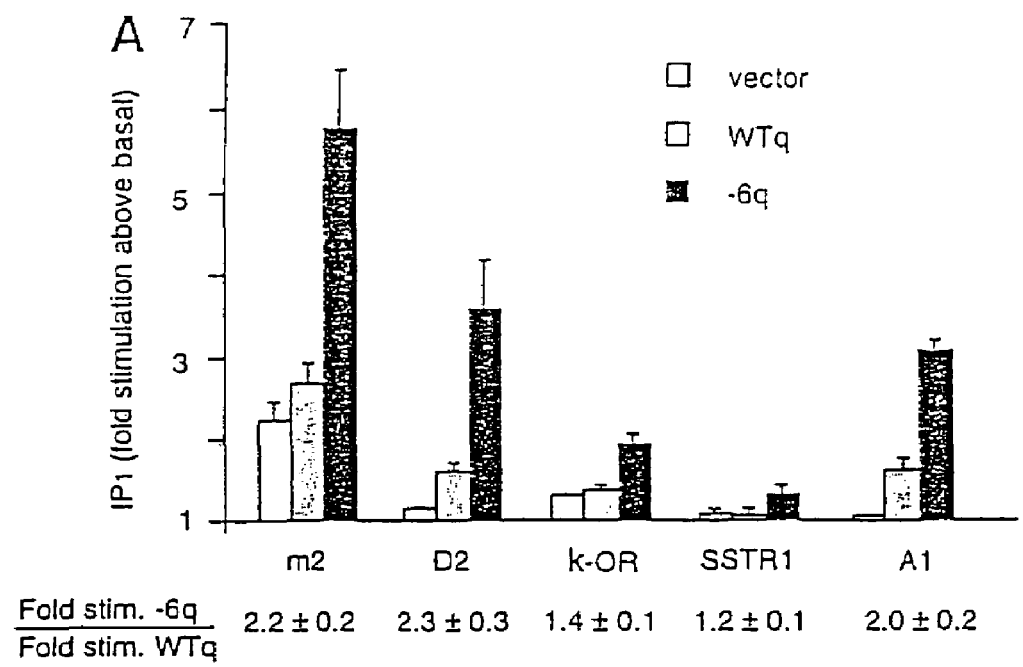
FIG. 2 shows a stimulation of the PLCβ signal transduction pathway by means of the –6q-Gα protein variation by Gi/o-coupled (A) and Gs-coupled (B) receptors using the maximum concentration of the relevant agonist.
Figure 2:
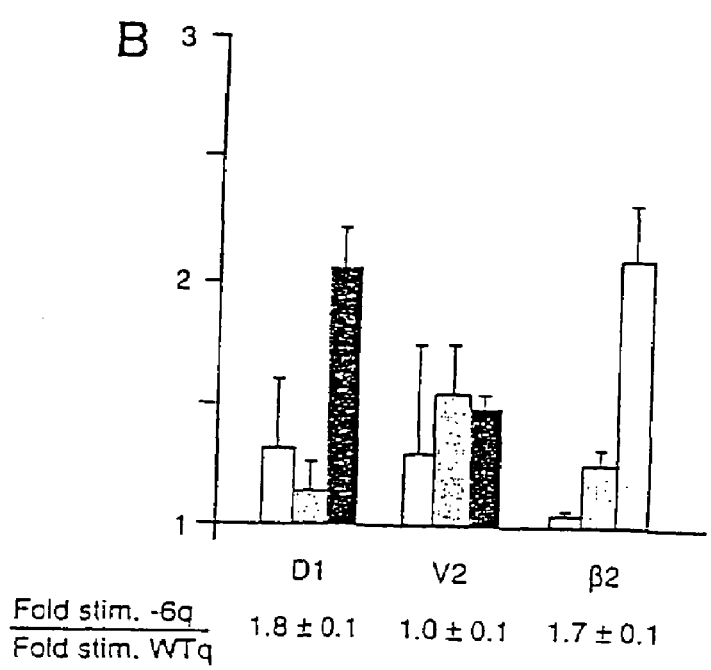

The action of at least one G-protein-coupled receptor (GPCR)-dependent signal transduction pathway of an organism can be modified in an inhibiting or stimulating manner by a chemical compound. A chemical compound presents an inhibiting effect if the signal transduction pathway-dependent measurable signal is weaker in the presence of the chemical compound than in its absence. Compounds evoking such an effect are called antagonists. A chemical compound presents a stimulating effect if the signal transduction pathway-dependent measurable signal is stronger in the presence of the chemical compound than in its absence. Such compounds are called agonists.

In one embodiment of the invention, the process makes use of a cell which produces at least two G-proteins. Said G-proteins may depend on one or on different GPCRs. In principle, all G-proteins are suitable for carrying out the process according to the invention, regardless of their receptor specificity, their sequence, their structure, the species for which they are specific, or the cell, tissue or organ from which they originate.

In one embodiment, cells producing at least one G-protein from among –6qi4myr, –6qs5myr, –6qi4, –6qs5 are used. The G-proteins –6qi4myr, –6qs5myr, –6qi4, –6qs5 are hybrid G-proteins assembled from portions of different mouse G-proteins, in some cases, containing additional modifications. The G-proteins may be produced by the cell individually or in combination. Apart from the hybrid G-proteins already mentioned, a cell may produce Gα16. Further, each of the G-proteins may be present in a cell individually or in combination with one or more other G-proteins. Gα16 should always be produced in a cell in combination with another of the G-proteins mentioned above.

The names and amino acid sequences of some example G-proteins according to the invention are as follows:—6qi4myr, SEQ ID NO:2;–6qs5myr, SEQ ID NO: 4;–6qi4. SEQ ID NO: 6;–6qs5, SEQ ID NO: 8, and Gα16, SEQ ID NO: 10.

The chemical compound is commonly provided in soluble form, for example dissolved in water. Besides the solvent, the solution may contain buffer substances, salts, or auxiliaries such as solubilizers, detergents, preservatives, or other substances.

Provision of a cell includes its production, cultivation, and processing. Cells are provided, for example, by preparing suitable cell material from organs or tissues, or by propagating suitable cell lines or microorganisms. Various suitable culture media can be used for cultivation. The cells are maintained at the optimum temperature for the organism from which they are provided. Where appropriate, preservatives, antibiotics, pH indicators, blood serum components, blood serum, auxiliaries, or other substances are added to the growth medium. Processes for production, cultivation and further processing are described in standard textbooks (One example: Basic Cell Culture; Ed. J. M. Davis; IRL Press; 1994).

In some embodiments of the process described above, the cell of a vertebrate, insect, or yeast species, or of *Caenorhabditis elegans* (*C. elegans*) is provided. In some embodiments, a HeLa, 293, COS, or CHO cell, or a *Saccharomyces cerevisiae* cell is provided.

In one embodiment of the invention, the intracellular $Ca^{2+}$ concentration is used as a signal transduction pathway-dependent measurable signal for determining the quantitative or qualitative effect of a chemical compound to be studied on a cell signal transduction pathway. The change in intracellular $Ca^{2+}$ concentration can be detected, for example, by using aequorin, a dye, or by the FLIPR™ technique from Molecular Devices Corp. (1311 Orleans Ave., Sunnyvale, Calif. 94089; 800-635-5577).

In another embodiment, the processes as described above may be used for identifying a pharmaceutical.

The invention also relates to at least one chemical compound which modifies the action of at least one G-protein-coupled receptor (GPCR)-dependent signal transduction pathway of an organism, with said chemical compound being identified by at least one process of this invention. Such chemical compounds could include, for example, hormones, scents, or pharmaceuticals that alter the chemical structure of hydrophilic signal substances which induce GPCRs.

The invention further relates to a polynucleotide sequence coding for a polypeptide having the property of a G-protein, which comprises a polypeptide selected from:
  a) a polypeptide having an amino acid sequence according to SEQ ID NO:2, SEQ ID NO:4, SEQ ID NO:6 or SEQ ID NO:8;
  b) a polypeptide according to a) lacking one or more amino acids;
  c) a polypeptide according to a) having an additional one or more amino acids;
  d) an allelic variant of the polypeptide according to a).

The allelic variants include polypeptides comprising a polynucleotide sequence of an allelic variant of the corresponding gene. An allelic variant of a gene is an alternate form occupying the same locus in a particular chromosome or linkage structure and differing from other alleles of the locus at one or more mutational sites.

In addition, the invention relates to a polynucleotide comprising a polynucleotide sequence selected from:
  a) a polynucleotide sequence according to SEQ ID NO:1, SEQ ID NO:3, SEQ ID NO:5 or SEQ ID NO:7 or the corresponding sequence complementary thereto;
  b) a polynucleotide sequence hybridizing with a polynucleotide sequence according to a) under stringent conditions.

The stringency is determined by the temperature and salt content. By varying the stringency, it is possible to adjust the extent of base pairing of two homologous nucleotide sequences. The extent of base pairing also depends on the length and base composition of a polynucleotide. Stringent conditions in accordance with this invention are present if 95% or more of the polynucleotide sequence and the hybridizing sequence are complementary.

In one embodiment of a polynucleotide sequence or a polynucleotide as described above, the polynucleotide is part of a recombinant vector construct. Recombinant vector constructs may be prepared with the help of knowledge in the art as illustrated, for example, in F. M. Ausubel et al., Current Protocols in Molecular Biology, Wiley &Sons, New York. The preparation entails inserting a polynucleotide coding for an amino acid sequence according to the sequence information described above (SEQ ID NO:2, 4, 6, or 8) or a polynucleotide sequence according to the sequence information described above (SEQ ID NO:1, 3, 5, or 7) into a base vector. A base vector is a vector into which a polynucleotide sequence can be inserted using molecular biology methods, and which can be cloned in a microorganism, for example, a bacterial, fungal, or cell culture cell. The base vector may comprise, for example, a phage, phagemid, plasmid, cosmid, viral, yeast artificial chromosome (YAC) or other type of vector. Non-limiting examples of base vectors are pUC18, pUC19, pBluescript, pKS, and pSK. The base vector may comprise, for example, a plasmid having an antibiotic resistance marker, an origin of replication suitable for propagating the plasmid in bacteria or cell cultures, and a promoter suitable for expressing the genes comprised in the inserted polynucleotide sequence. The polynucleotide sequence is inserted via suitable restriction cleavage sites using appropriate restriction enzymes commercially available from companies such as New England BioLabs, Roche Diagnostics, Stratagene, and others. Such restriction cleavage sites may be those of the restriction enzymes BamHI, EcoRI, SalI, and EcoRV, for example.

In another embodiment, the recombinant vector construct comprises an expression vector usable in eukaryotes and/or prokaryotes. An expression vector contains a promoter which can be linked functionally to a polynucleotide sequence so that a protein encoded by said polynucleotide sequence is synthesized in a microorganism, for example, such as a bacterium or a fungus, or in the cell of a eukaryotic cell line. The promoter may be inducible, by means of tryptophan for example, or may be constitutive. Some non-limiting examples of expression vectors are pUC18, pUC19, pBluescript, and pcDNA3.1.

The invention further relates to a host cell which may comprise a polynucleotide or a recombinant vector construct as described above. In one embodiment, the host cell comprises a human cell. In other embodiments, the host cell comprises the cell of a vertrebrate, insect, bacterium, or yeast species, or *C. elegans*. In yet other embodiments, the cell comprises a HeLa, 293, COS or CHO cell, or an *Escherichia coli* or *Saccharomyces cerevisiae* cell. Other eukaryotic cells or cell lines, or other bacteria, such as *Bacillus* or *Streptomyces* species, and fungi, such as *Penicillium* or *Aspergillus* species, may also be used.

The invention also relates to the production of a host cell as described above by introducing a polynucleotide according to one or more of the polynucleotide sequences as disclosed in SEQ ID NO: 1, 2, 3, 4, 5, 6, 7, and 8 or a recombinant vector construct as characterized above into a eukaryotic or prokaryotic cell. The polynucleotide sequences may be introduced for example, by electroporation, by $Ca^{2+}$ phosphate precipitation of the eukaryotic or prokaryotic cells together with the polynucleotide sequence, or by other transformation methods.

A host cell of this kind may be used for carrying out an above-described process of this invention.

The invention also relates to a protein having an amino acid sequence selected from: SEQ ID NO:2, SEQ ID NO:4, SEQ ID NO:6, and SEQ ID NO:8.

Moreover, the invention relates to a process for preparing a protein comprising an amino acid sequence selected from SEQ ID NO:2, SEQ ID NO:4, SEQ ID NO:6, and SEQ ID NO:8, wherein the process comprises the following steps:
 a) producing a host cell containing an appropriate polynucleotide sequence and prepared as described above;
 b) cultivating said host cell in a growth medium suitable for the host cell and inducing expression of the protein encoded by the polynucleotide sequence;
 c) obtaining the cell material and disrupting the cells;
 d) removing the protein by means of biochemical methods for protein purification.

For preparing and purifying the proteins denoted, known methods, as described in F. M. Ausubel et al., Current Protocols in Molecular Biology, Wiley & Sons, New York, may be used accordingly.

A protein having an amino acid sequence according to SEQ ID NO:2, 4, 6, or 8 or prepared according to the process described may be used for producing antibodies.

EXAMPLES

Example 1

Activation of a Signal Transduction Pathway via the Gα-Protein Mutant −6q by Various Receptors COS7 cells were cultured in DMEM (Dulbecco's modified Eagle's medium) with 10% FCS (fetal calf serum) at 37° C. (5% $CO_2$). For transfections, $1 \times 10^6$ cells were seeded in 100-mm plates. About 24 hours later, the cells were cotransformed with the expression plasmids αq or −6q (1 μg DNA/100 mm plate) and, in each case, one of the following receptor constructs (4 μg DNA/100 mm plate): M2 (muscarinic receptor in pCD), D2 (dopamine receptor in pCD-NAI), kappa (opioid receptor in pCDNA3), SSTR1 (somatostatin receptor in pCMV), A1 (adenosine receptor in CDM7), D1 (dopamine receptor in pCNAI), V2 (vasopressin receptor in pCD-ps), β2 (adrenergic receptor in pSVL).

About 24 hours after transfection, the cells were divided into equal portions in 6-well plates and 3 μCi/ml $^3$H-myo-inositol (20 Ci/mmol) in DMEM was added. After incubation for 24 hours, the cells were incubated with HBSS (Hank's Balanced Salt Solution; +10 mM LiCl) at room temperature for 20 minutes. The cells were then stimulated with the appropriate agonists for one hour, and the increase in intracellular inositol monophosphates (IP1) was determined by anion exchange chromatography. IP1 is a signal molecule, that is generated in the PLC-β-signal transduction pathway and leads in the further course of the signal transduction to an increase in intracellular $Ca^{2+}$ concentration.

The results which follow were obtained with the Gα-protein construct −6q. Compared with the wild-type sequence (WTq), denoted αq in FIG. 1, this mutant lacks the six highly conserved amino acid residues at the amino-terminal end, as depicted in FIG. 1. Moreover, FIG. 1 presents additional sequence examples. Mutants of this kind and receptor constructs used were prepared with the aid of standard molecular biological methods, as described in detail, for example in F. M. Ausubel et al., Current Protocols in Molecular Biology, Wiley & Sons, New York.

COS7 cells expressing WTq or −6q various Gi/o-coupled receptors (A) or Gs-coupled receptors (B) were incubated (37° C.) in the presence and absence of the appropriate agonists (see below) for 1 hour. The increase in intracellular IP1 concentration was determined as described above. The data represent averages ±S.E. of 3-7 independent experiments, with each determination performed in triplicate. The following ligands were used:

FIG. 2 A: m2 (muscarinic receptor): carbachol (100 μM); D2 (dopamine receptor): (−)-quinpirole (10 μM); K-OR (kappa (opioid receptor)): (−)-U50488 (10 μM); SSTR1 (somatostatin receptor): somatostatin14 (1 μM); B, A1 (adenosine receptor): R(−)-PIA (10 mM);

FIG. 2 B: D1 (dopamine receptor): dopamine (1 mM); V2 (vasopressin receptor): AVP (1 nM); β2 (adrenergic receptor): (−)-isoproterenol (200 μM). The numbers below the figures indicate the extent of the particular PLC stimulation as relative increase in PLC stimulation from −6q to WTq.

FIG. 2 shows that the Gα-protein mutant −6q stimulates IP1 formation depending on different receptor classes. The experimental results for −6q in FIG. 2 are compared with stimulation of IP1 by means of the wild-type construct (WTq) and with the vector construct without any Gα insert (vector). IP1 release by means of the −6q construct succeeds both with Gi/o-coupled (FIG. 2 A: m2, D2, k-OR, SSTR1, A1) and with Gs-coupled (FIG. 2 B: D1, V2, β2) receptors.

Example 2

Preparation of Highly Expressed Mutants of Gα Proteins with Broad Receptor Specificity Hybrid G-protein α subunits, that lack the six highly conserved amino acids of the amino terminus and that simultaneously have either an αi or αs sequence at the C terminus were constructed. They are denoted −6qi4 or −6qs5, corresponding to the αi sequence or αs sequence they contain. The construct −6qi4 links the Gs-coupled receptors and also some of the Gi/o-coupled receptors, such as the SSTR1 and edg5 receptors, to the PLCβ signal transduction pathway. Gα16 cannot link the edg5 receptor to the PLCβ signal transduction pathway. Gα16 is a G-protein with broad receptor specificity and has been disclosed in WO 97/48820 (title: Promiscuous G-protein compositions and their use).

The construct −6qs5 links the Gi/o-coupled receptors and the Gs-coupled receptors to the PLCβ signal transduction pathway and also recognizes receptors such as the dopamine D1 receptor or the adrenergic β2 receptor.

A combination of the two G-protein α subunits −6qi4 and −6qs5 in one cell line thus recognizes a wider range of GPCRs than each subunit separately or than Gα16.

The applicability of −6qi4 and −6qs5 Gα subunits in technical screening procedures could be further improved if their expression were increased, because this would result in a stronger signal.

Figure 3:
FIG. 3 shows an SDS-PAGE Western blot with increased expression of –6qi4myr in comparison with –6qi4. The expression of other Gα proteins is also shown.
Figure 4:
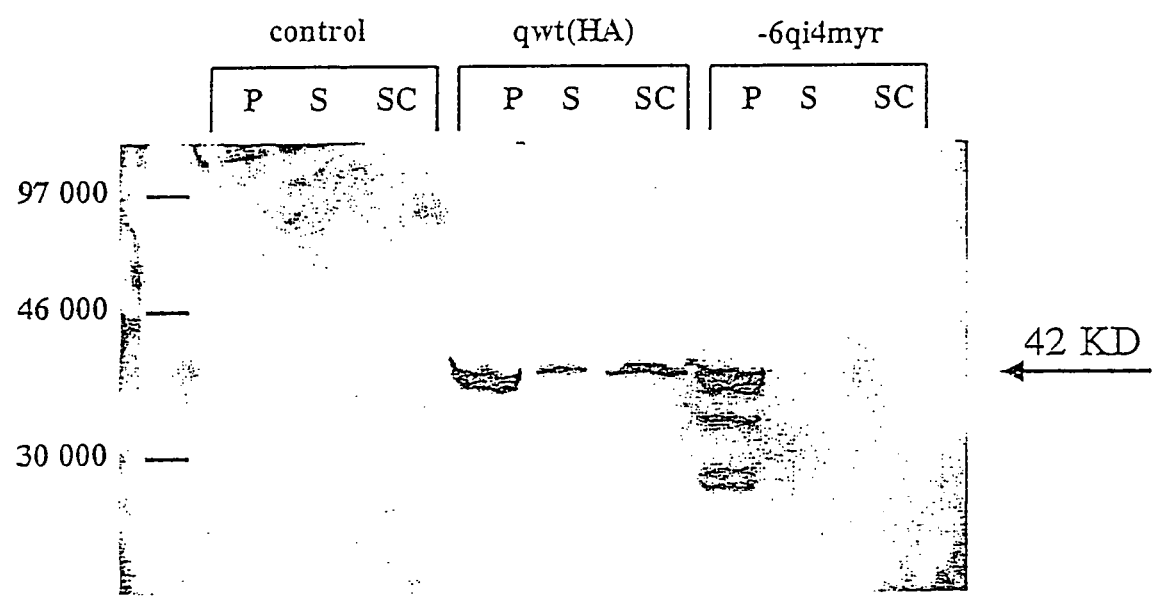
FIG. 4 depicts an SDS-PAGE Western blot showing fractionation of qWT and –6qi4myr into a membrane-containing particle fraction (P) and a soluble fraction (S; SC). The G-protein α subunits were detected by the 12CA5 monoclonal antibody resulting in protein bands of ~42 KD.

For this reason, additional myristoylation/palmitoylation recognition sequences were inserted into the amino-terminal region of the Gα subunits to produce –6qi4myr and –6qs5myr from –6qi4 and –6qs5, respectively. The protein sequence of –6qimyr and –6qs5myr at the amino terminus is MGCC (residues 1-4 of SEQ ID NOs: 2 and 4. respectively), in contrast to MACC (residues 1-4 of SEQ ID NOs: 6 and 8, respectively) in the original sequence of the 6q variants. Therefore, the novel constructs, –6qi4myr and –6qs5myr, contain a consensus sequence for myristoylation/palmitoylation. It is known that removing myristyl or palmityl residues from G-proteins leads to a redistribution in the cell. Loss of palmitate or myristate residues influences the expression pattern of the G-proteins in such a way that G-protein α subunits are found both in the cell membrane and in the cytosol, but are mainly cytosol-localized. However, only the membrane-bound G-proteins can pass the signals from GPCRs on to intracellular effectors. Only the consequences of removing a consensus sequence for polmitoylation/myristoylation by mutation were known. It was not known if introducing an additional consensus site for yristoylation/palmitoylation into the Gα deletion mutants would affect expression. However, it was possible to show that introducing additional polmitoylation/myristoylation sites increases the amount of Gα subunits expressed in the cell membrane (FIG. 3, FIG. 4). The SDS-PAGE Western blot (sodium dodecyl sulfate polyacrylamide gel electrophoresis Western blot) in FIG. 3 shows distinctly increased expression of –6qi4myr compared to –6qi4. FIG. 4 depicts an SDS-PAGE Western blot of a fractionation of qwt and –6qi4myr into a membrane-containing particle fraction (P) and a soluble fraction (S; SC). The variant with a higher degree of myristoylation/palmitoylation, –6qi4myr, is present only in the particle fraction.

For the SDS-PAGE Western blot, all G-protein α subunits were detected by the 12CA5 monoclonal antibody (coupled to horseradish peroxidase; Roche Biosciences), which is directed against the HA epitope tag contained in all of the G-protein constructs (generally the peptide sequence YPYDVPDYA). In qWT the HA tag replaces amino acids 125-130, while in the N-terminally deleted G-proteins (–6q, –6qi4, –6qi4myr) it replaces amino acids 119-124.20 μg of membrane protein, prepared from transfected COS7 cells, were in each case fractionated by means of SDS PAGE gel electrophoresis (for example, at 10% polyacrylamide) and blotted onto nitrocellulose, and the G-protein α subunits were detected by the 12CA5 antibody. Immunoreactive G-proteins were visualized using a chemiluminescence system (Amersham).

Figure 5:
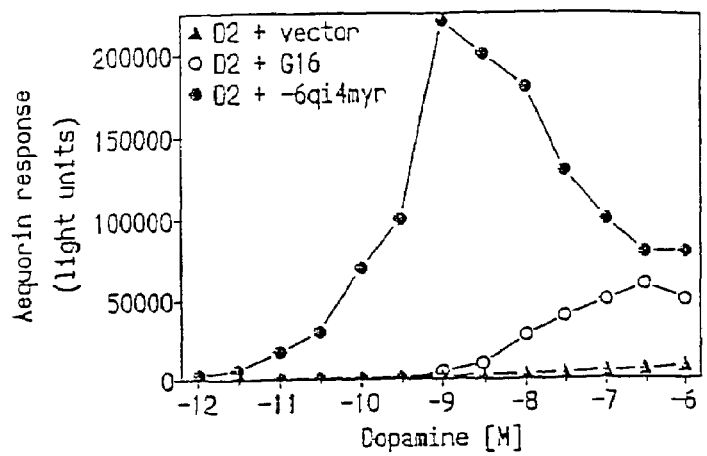
FIG. 5 shows the linking of various Gi/o-coupled receptors to the PLCβ signal transduction pathway by –6qi4myr. D2, KOR and SSTR1 are Gi/o-coupled receptors. The controls used were a vector construct and the Gα16 protein (G16).
Figure 5:
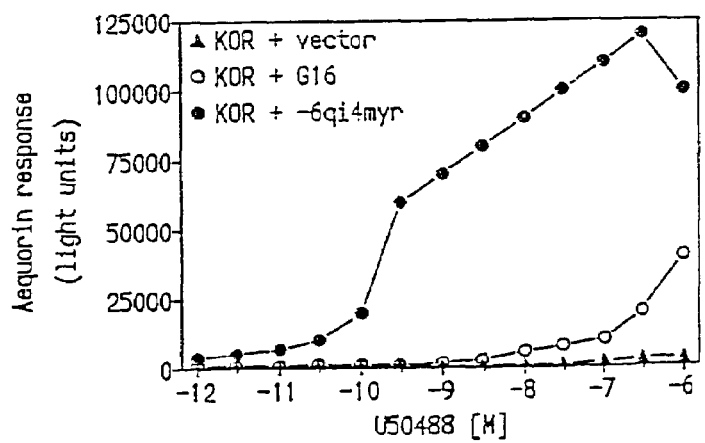
Figure 5:
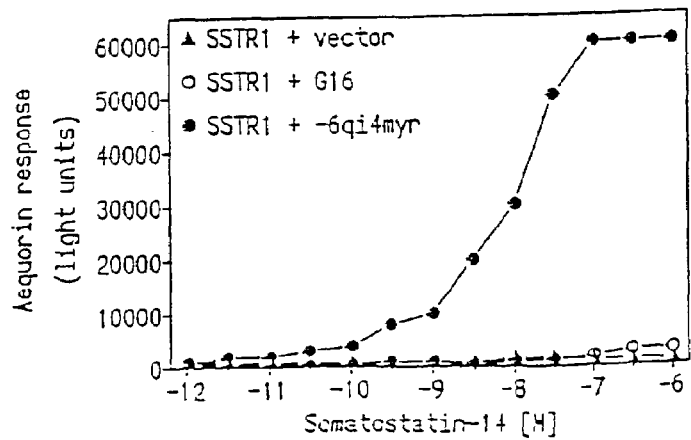
Figure 6:
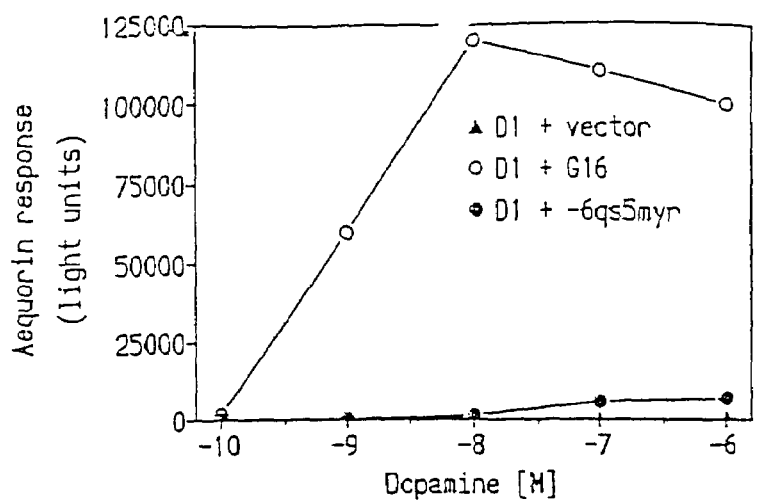
FIG. 6 shows that Gs-coupled receptors are linked to the PLCβ signal transduction pathway by –6qs5myr. β1, β2 and D1 are Gs-coupled receptors. A vector construct and the G-protein Gα16 (G16) serve as references.
Figure 6:
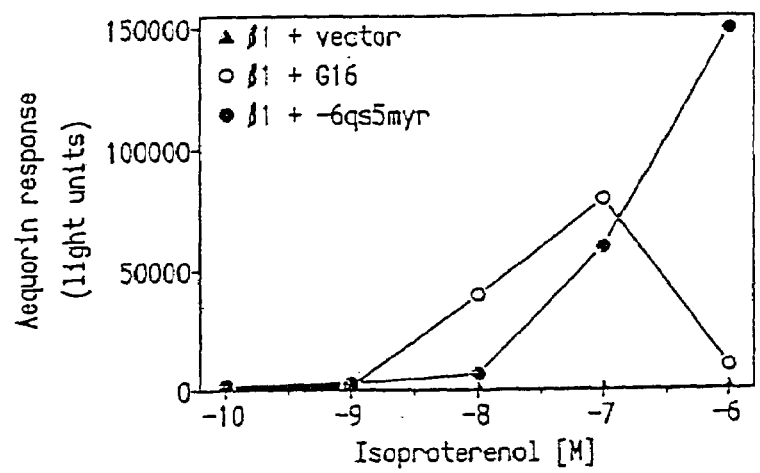
Figure 6:
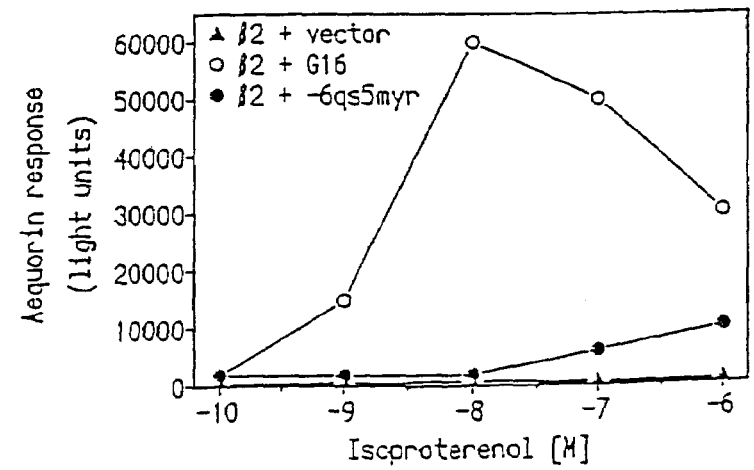
Figure 7:
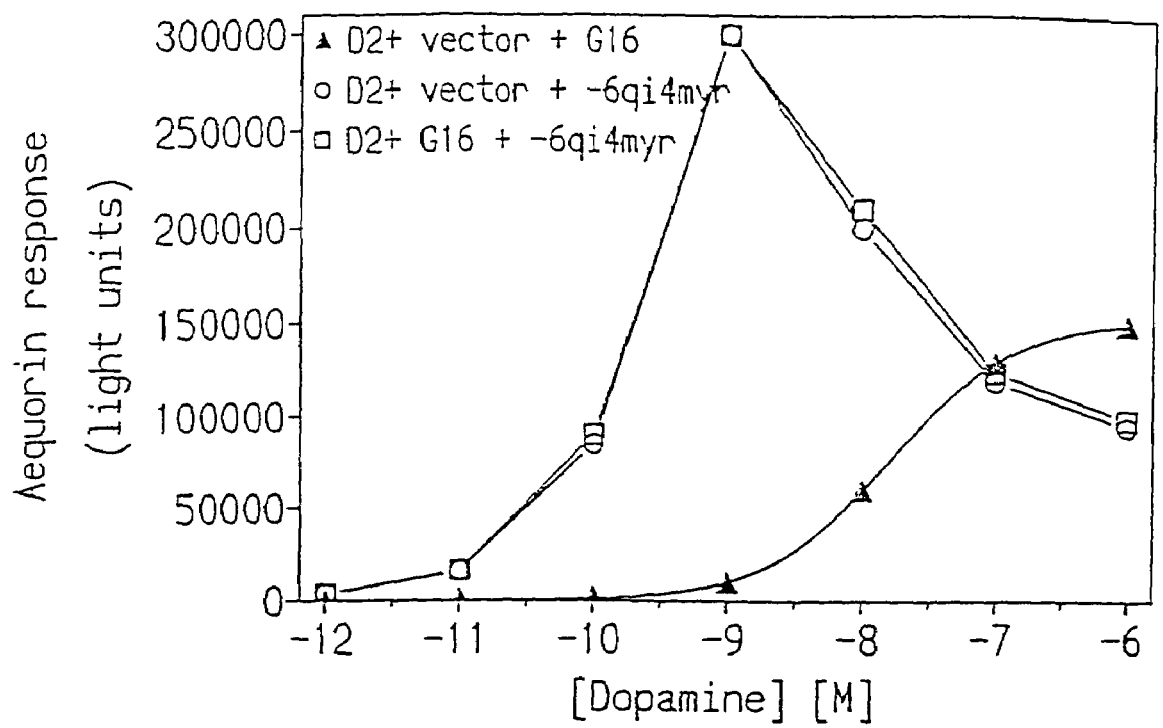
FIG. 7 shows the linking of the Gi/o-coupled dopamine D2 receptor to the PLCβ-$Ca^{2+}$ signal transduction pathway in the presence of the low-sensitivity α subunit Gα16 (G16), in the presence of the very sensitive Gα subunit –6qi4myr and in the presence of a combination of Gα16 and –6qi4myr. It is evident that the potential activation of calcium release by –6qi4myr is not adversely affected by the presence of Gα16.

Example 3:

Stimulation of Various Highly Expressed Gα-Proteins with Broad Receptor Specificity by Different Receptors Stimulation of the highly expressed Gα variants, –6qs5myr and –6qi4myr, by different receptors is depicted in FIG. 5 and FIG. 6. FIG. 5 shows that –6qi4myr is connected by Gi/o-coupled receptors (for example, dopamine D2, edg5, CCR5, SSTR1, and KOR) to the PLCβ signal transduction pathway and leads to a strong signal which is proportional to $Ca^{2+}$ release. The controls used were a vector construct and the Gα16 protein (G16). FIG. 6 shows that Gs-coupled receptors are linked to the PLCβ signal transduction pathway by –6qs5myr. The G-protein Gα16 (G16) acted as a control.

To experimentally determine the released $Ca^{2+}$ concentration with the aequorin system, CHO cells were cotransfected with the apo-aequorin expression plasmid cytAEQ/pCDNAI, the receptor DNA mentioned above (for example, SSTR1, KOR, D2, D1, or β2) and the G-protein α subunits Gα16 and –6qi4myr with the use of lipofectamine. After incubation in OPTIMEM medium for 10 hours, the cells were washed once with RPMI 1640 medium and incubated with 5 μM coelenterazine f in RPMI 1640 at 37° C. for 2 hours. The cells were then washed twice with PBS and stimulated using the appropriate receptor agonists: somatostatin 14 for the SSTR1 receptor, U50488 for the kappa opioid receptor, (–)-quinpirole for the dopamine D2 receptor, dopamine for the dopamine D1 receptor and isoproterenol for the β2 receptor. Agonist stimulation of Gi/o-coupled receptors (SSTR1, KOR, and D2) and Gs-coupled receptors (D1 and β2) leads to activation of the G-proteins Gα16 and –6qi4myr followed by stimulation of PLCβ and intracellular $Ca^{2+}$ release. $Ca^{2+}$ binding to the apo-aequorin-coelenterazine complex leads to light emission which was measured using a luminometer (TOPCOUNT®, Hewlett Packard).

What is claimed is:

1. A process for identifying a chemical compound modifying the action of at least one G-protein-coupled receptor (GPCR)-dependent signal transduction pathway of an organism, wherein said process comprises the following steps:
   a) providing at least one cell which contains at least one GPCR-dependent signal transduction pathway and which produces one or more than one myristoylated −6q G protein hybrid;
   b) providing at least one chemical compound to be studied;
   c) contacting the cell of a) with one or more of the chemical compounds of b);
   d) determining the quantitative or qualitative effect of the chemical compound or compounds of b) on the signal transduction pathway of the cell of a) by means of a signal transduction pathway-dependent measurable signal.

2. The process as claimed in claim 1, wherein the cell provided according to a) produces at least two G-proteins.

3. The process as claimed in claim 1, wherein the cell provided according to a) produces at least one protein having an amino acid sequence selected from SEQ ID NO:2 and SEQ ID NO:4.

4. The process as claimed in claim 3, wherein the intracellular $Ca^{2+}$ concentration is the signal transduction pathway-dependent measurable signal.

5. The process as claimed in claim 4, wherein the process is used for identifying a pharmaceutical.

6. The process as claimed in claim 3, wherein the process is used for identifying a pharmaceutical.

7. The process as claimed in claim 1, wherein the cell provided according to a) is the cell of a vertebrate species, an insect species, a yeast species, or a *C. elegans*.

8. The process as claimed in claim 7, wherein the cell provided is a HeLa, 293, COS or CHO cell, or a cell of *Saccharomyces cerevisiae*.

9. The process as claimed in claim 8, wherein the intracellular $Ca^{2+}$ concentration is the signal transduction pathway-dependent measurable signal.

10. The process as claimed in claim 9, wherein the process is used for identifying a pharmaceutical.

11. The process as claimed in claim 8, wherein the process is used for identifying a pharmaceutical.

12. The process as claimed in claim 7, wherein the intracellular $Ca^{2+}$ concentration is the signal transduction pathway-dependent measurable signal.

13. The process as claimed in claim 12, wherein the process is used for identifying a pharmaceutical.

14. The process as claimed in claim 7, wherein the process is used for identifying a pharmaceutical.

15. The process as claimed in claim 1, wherein the intracellular $Ca^{2+}$ concentration is the signal transduction pathway-dependent measurable signal.

16. The process as claimed in claim 15, wherein the process is used for identifying a pharmaceutical.

17. The process as claimed in claim 1, wherein the process is used for identifying a pharmaceutical.

18. The process as claimed in claim 2, wherein the cell provided according to a) produces at least one protein having an amino acid sequence selected from SEQ ID NO:2 and SEQ ID NO:4.

19. The process as claimed in claim 18, wherein the intracellular $Ca^{2+}$ concentration is the signal transduction pathway-dependent measurable signal.

20. The process as claimed in claim 19, wherein the process is used for identifying a pharmaceutical.

21. The process as claimed in claim 18, wherein the process is used for identifying a pharmaceutical.

22. The process is claimed in claim 2, wherein the intracellular $Ca^{2+}$ concentration is the signal transduction pathway-dependent measurable signal.

23. The process as claimed in claim 22, wherein the process is used for identifying a pharmaceutical.

24. The process as claimed in claim 2, wherein the process is used for identifying a pharmaceutical.

25. The process as claimed in claim 1 or claim 2, wherein the cell provided according to a) produces the myristoylated −6q G protein hybrid wherein said hybrid is selected from the group consisting of −6qi4myr and −6qs5myr.

26. The process as claimed in claim 25, wherein the cell provided according to a) produces at least one protein having an amino acid sequence selected from SEQ ID NO:2 and SEQ ID NO:4.

27. The process as claimed in claim 26, wherein the intracellular $Ca^{2+}$ concentration is the signal transduction pathway-dependent measurable signal.

28. The process as claimed in claim 27, wherein the process is used for identifying a pharmaceutical.

29. The process as claimed in claim 26, wherein the process is used for identifying a pharmaceutical.

30. The process as claimed in claim 25, wherein the intracellular $Ca^{2+}$ concentration is the signal transduction pathway-dependent measurable signal.

31. The process as claimed in claim 30, wherein the process is used for identifying a pharmaceutical.

32. The process as claimed in claim 25, wherein the process is used for identifying a pharmaceutical.

33. The process as claimed in claim 1 or claim 2, wherein the cell provided according to a) further produces a G$\alpha$16 G protein.

34. The process as claimed in claim 33, wherein the intracellular $Ca^{2+}$ concentration is the signal transduction pathway-dependent measurable signal.

35. The process as claimed in claim 34, wherein the process is used for identifying a pharmaceutical.

36. The process as claimed in claim 33, wherein the process is used for identifying a pharmaceutical.

* * * * *